US006441245B1

(12) United States Patent
Moriarty et al.

(10) Patent No.: US 6,441,245 B1
(45) Date of Patent: Aug. 27, 2002

(54) PROCESS FOR STEREOSELECTIVE SYNTHESIS OF PROSTACYCLIN DERIVATIVES

(75) Inventors: Robert M. Moriarty, Oak Park; Raju Penmasta, Bolingbrook; Liang Guo, Chicago; Munagala S. Rao, Westmont; James P. Staszewski, Naperville, all of IL (US)

(73) Assignee: United Therapeutics Corporation, Washington, DC (US)

( * ) Notice: Subject to any disclaimer, the term of this patent is extended or adjusted under 35 U.S.C. 154(b) by 0 days.

(21) Appl. No.: 09/541,521

(22) Filed: Apr. 3, 2000

Related U.S. Application Data

(63) Continuation-in-part of application No. 09/481,390, filed on Jan. 12, 2000, which is a continuation of application No. 08/957,736, filed on Oct. 24, 1997, now abandoned.

(51) Int. Cl.$^7$ ............................................. C07C 49/537
(52) U.S. Cl. ...................... 568/379; 568/338; 560/121; 562/503
(58) Field of Search ................................ 568/308, 309, 568/311, 316, 322, 327, 734, 807, 808, 632, 633, 634, 715, 379, 338; 569/381, 506, 41, 42, 44, 49; 560/56, 121; 562/503

(56) References Cited

U.S. PATENT DOCUMENTS

| 4,306,075 A | 12/1981 | Aristoff |
| 5,153,222 A | 10/1992 | Tadepalli et al. |

FOREIGN PATENT DOCUMENTS

| EP | 0 087 237 A1 | 8/1983 |
| WO | WO 98/39337 | 9/1998 |

OTHER PUBLICATIONS

J. J. F. Belch et al., Circulation, vol. 95, No. 9, "Randomized, Double–Blind, Placebo–Controlled Study Evaluating the efficacy and Safety of AS–013, a prostaglandin $E_1$ Prodrug, in Patients With Intermittent Claudication," pp. 2298–2302 (1997).
N. A. Nelson, Journal of Medicinal Chemistry, vol. 17, No. 9, "Prostaglandin Nomenclature," pp. 911–918 (1974).
S. Takano et al., Chemistry Letters, "Enantiodivergent Synthesis of Both Enantiomers of Sulcatol and Matsutake Alcohol from ®–Epichlorohydrin," pp. 2017–2020 (1987).
D. J. Mathre et al., J. Org. Chem., vol. 56, "A Practical Enantioselective Synthesis of α,α–Diaryl–2–pyrrolidinemethanol, Preparation and Chemistry of the Corresponding Oxazaborolidines," pp. 751–762 (1991).
B. L. Pagenkoph, Diss. Abstr. Int., vol. 57, No. 12, "Substrate and reagent control of diastereoselectivity in transition metal–mediated process: development of a catalytic photo promoted Pauson–Khand reaction," p. 7535 (1997) Abstract XP–002097925.
J. Mulzer et al., Liebigs Ann. Chem., vol. 9, "Asymmetric Synthesis of Carbacyclin Precursors by Pauson–Khand Cyclization," pp. 891–897 (1988) Abstract XP–002097924.
I. U. Khand et al., J. Chem. Soc., Perkin Trans., "Organocobalt Complexes. Part II. Reaction of Acetylenehexacarbonyldicobalt Complexes, $(R^1C_2R^2)Co_2(CO)_6$, with Norbornene and its Derivatives," pp. 977–981 (1973).
P. L. Pauson, Tetrahedron, vol. 41, No. 24, "A Convenient and General Route to a Wide Range of Cyclopentenone Derivatives," pp. 5855–5860 (1985).
N. E. Schore, Chem. Rev., vol. 88, "Transition–Metal–Medicatied Cycloaddition Reactions of Alkynes in Organic Synthesis," pp. 1081–1119 (1988).
S. Shambayati et al., Tetrahedron Letters, vol. 31, "N–Oxide Promoted Pauson–Khand Cyclizations at Room Temperature," pp. 5289–5292 (1990).
Y. K. Chung et al., Organometallics, vol. 12, "Promoters for the (Alkyne)hexacarbonyldicobalt–Based Cyclopentenone Synthesis," pp. 220–223 (1993).
N. Jeong et al., J. Am. Chem. Soc., vol. 116, "Catalytic Version of the Intramolecular Pauson–Khand Reaction," pp. 3159–3160 (1994).
F. A. Hicks et al., J. Org. Chem., vol. 61, "A practical Titanium–Catalyzed Synthesis of Bicyclic Cyclopentenones and Allylic Amines," pp. 2713–2718 (1996).
M. Zhang et al., J. Org. Chem., vol. 61, "A Nickel(0)–Catalyzed Process for the Transformation of Enynes to Bicyclic Cyclopentenones," pp. 4498–4499 (1996).
B. L. Pagenkopf et al., J. Am. Chem. Soc., vol. 118, "Photochemical Promotion of the Intramolecular Pauson–Khand Reaction. A New Experimental Protocol for Cobalt–Catalyzed [2+2+1] Cycloadditions," pp. 2285–2286 (1996).

*Primary Examiner*—Sreeni Padmanabhan
(74) *Attorney, Agent, or Firm*—Foley & Lardner

(57) ABSTRACT

An improved method is described for making 9-deoxy-$PGF_1$-type compounds. In contrast to the prior art, the method is stereoselective and requires fewer steps than the known methods for making these compounds.

10 Claims, No Drawings

PROCESS FOR STEREOSELECTIVE SYNTHESIS OF PROSTACYCLIN DERIVATIVES

This application is a continuation-in-part of U.S. Ser. No. 09/481,390, filed Jan. 12, 2000, which in turn is a continuation of U.S. Ser. No. 08/957,736, filed Oct. 24, 1997 now abandoned.

FIELD OF THE INVENTION

The present application relates to a process for producing prostacyclin derivatives and novel intermediate compounds useful in the process.

BACKGROUND OF THE INVENTION

Prostacyclin derivatives are useful pharmaceutical compounds possessing activities such as platelet aggregation inhibition, gastric secretion reduction, lesion inhibition, and bronchodilation.

For convenience, the novel prostacyclin derivatives will be referred to by the trivial, art-recognized system of nomenclature described by N. A. Nelson, J. Med. Chem. 17:911 (1974) for prostaglandins. Accordingly, all of the novel prostacyclin derivatives herein will be named as 9-deoxy-$PGF_1$-type compounds.

U.S. Pat. No. 4,306,075 discloses methods for making prostacyclin derivatives. However, these and other known processes involve a large number of steps. It is an object of the present invention to provide an improved method of preparing prostacyclin derivatives involving fewer steps.

SUMMARY OF THE INVENTION

The present invention relates to a process for preparing 9-deoxy-$PGF_1$-type compounds by a process that is stereoselective and requires fewer steps than the prior art. The invention also relates to novel intermediates prepared during the synthesis of the 9-deoxy-$PGF_1$-type compounds.

DETAILED DESCRIPTION OF THE PREFERRED EMBODIMENTS

In one embodiment, the present invention relates to an improved stereoselective method for making 9-deoxy-$PGF_1$-type compounds comprising converting a compound of the formula:

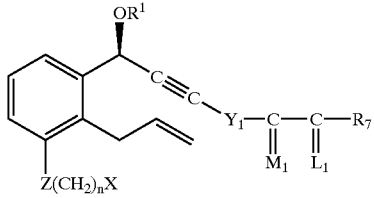

into a compound of the following formula:

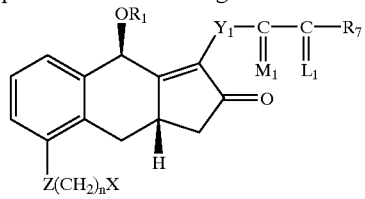

wherein Z is O, S, $CH_2$, or $NR_8$ in which $R_8$ is H, alkyl or aryl;

X is H, CN, $OR_9$, or $COOR_9$ in which $R_9$ is alkyl, THP or TBDMS;

wherein n is 0, 1, 2, or 3;

wherein $Y_1$ is trans-CH=CH—, cis-CH=CH—, —$CH_2$($CH_2$)$_m$—, or —C≡C—; m is 1, 2, or 3;

wherein $R_1$ is an alcohol protecting group;

wherein $R_7$ is (1) —$C_pH_{2p}$—$CH_3$, wherein p is an integer from one to 5, inclusive, (2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and R4 are hydrogen or methyl, being the same or different, (3) phenyl, benzyl, phenylethyl, or phenylpropyl optionally substituted on the aromatic ring by one, two or three chloro, fluoro, trifluoromethyl, ($C_1$–$C_3$) alkyl, or ($C_1$–$C_3$)alkoxy, with the proviso that not more than two substituents are other than alkyl, (4) cis-CH=CH—$CH_2$—$CH_3$, (5) —($CH_2$)$_2$—CH(OH)—$CH_3$, or (6) —($CH_2$)$_3$—CH=C($CH_3$)$_2$;

wherein —C($L_1$)—$R_7$ taken together is (1) ($C_4$–$C_7$)cycloalkyl optionally substituted by one to 3 ($C_1$–$C_5$) alkyl;

(2) 2-2-furyl)ethyl, (3) 2-3-thienyl)ethoxy, or (4) 3-thienyloxymethyl;

wherein $M_1$ is α-OH:β-$R_5$ or α-$R_5$:β-OH, wherein $R_5$ is hydrogen or methyl; and wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

Preferably, the above conversion is carried out through cobalt-mediated cyclization, in which a complex is formed with the alkynyl group of the starting compound, which decomposes upon heating to form a tricyclic structure. More preferably, this cyclization is carried out by reacting $Co_2(CO)_8$ with the above compound of the formula:

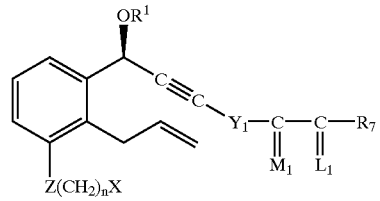

using a suitable non-reactive solvent. Preferably, the non-reactive solvent is a chlorinated solvent, a hydrocarbon solvent, or an aromatic solvent. More preferably, the non-reactive solvent is $CH_2Cl_2$, toluene, isooctane, and heptane.

In the case of carrying out the cobalt-mediated cyclization with $CH_2Cl_2$, after reacting $Co_2(CO)_8$ with the above compound of the formula:

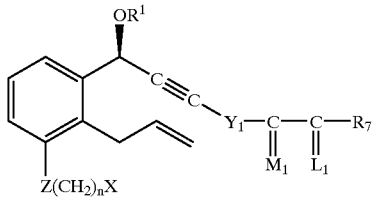

in the presence of $CH_2Cl_2$ to form a complex with the alkynyl group, preferably the $CH_2Cl_2$ is removed in a subsequent step and replaced with $CH_3CN$ followed by heating in an inert gas atmosphere, such as argon, nitrogen, or carbon monoxide, which decomposes the complex to form the above tricyclic compound.

Although $Co_2(CO)_8$ contributes a carbonyl during the reaction, it is not necessary to react equal amounts of the starting compound of the above formula and $Co_2(CO)_8$. It is also possible to use the $Co_2(CO)_8$ in a catalytic way, by introducing a relatively small amount of $Co_2(CO)_8$ and also introducing CO into the reaction mixture (e.g., by bubbling CO into the reaction mixture) in the presence of light which catalyzes the transfer of CO through a Co-mediated complex formed with the above compound of the formula:

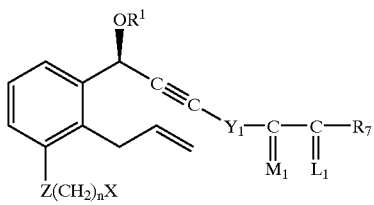

In another preferred embodiment, the present invention relates to an improved stereoselective method for making 9-deoxy-$PGF_1$-type compounds comprising the following reaction:

wherein n is 0, 1, 2 or 3;

wherein $Y_1$ is trans-CH=CH—, cis-CH=CH—, —$CH_2$($CH_2$)$_m$—, or —C≡C—; m is 1, 2, or 3;

wherein $R_1$ is an alcohol protecting group;

wherein $R_7$ is (1) —$C_pH_{2p}CH_3$, wherein p is an integer from one to 5, inclusive, (2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different, (3) phenyl, benzyl, phenylethyl, or phenylpropyl optionally substituted on the aromatic ring by one, two or three chloro, fluoro, trifluoromethyl, ($C_1$–$C_3$) alkyl, or ($C_1$–$C_3$)alkoxy, with the proviso that not more than two substituents are other than alkyl, (4) cis-CH=CH—$CH_2$—$CH_3$, (5) —$(CH_2)_2$—CH(OH)—$CH_3$, or (6) —$(CH_2)_3$—CH=C$(CH_3)_2$;

wherein —C($L_1$)—$R_7$ taken together is (1) ($C_4$–$C_7$)cycloalkyl optionally substituted by one to 3 ($C_1$–$C_5$) alkyl;

(2) 2-(2-furyl)ethyl, (3) 2-(3-thienyl)ethoxy, or (4) 3-thienyloxymethyl;

wherein $M_1$ is α-OH:β-$R_5$ or α-$R_5$:β-OH, wherein $R_5$ is hydrogen or methyl;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

The present invention also relates to a method of making the following compounds utilizing the foregoing reaction:

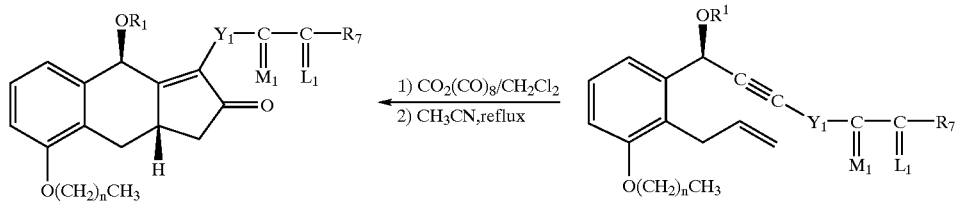

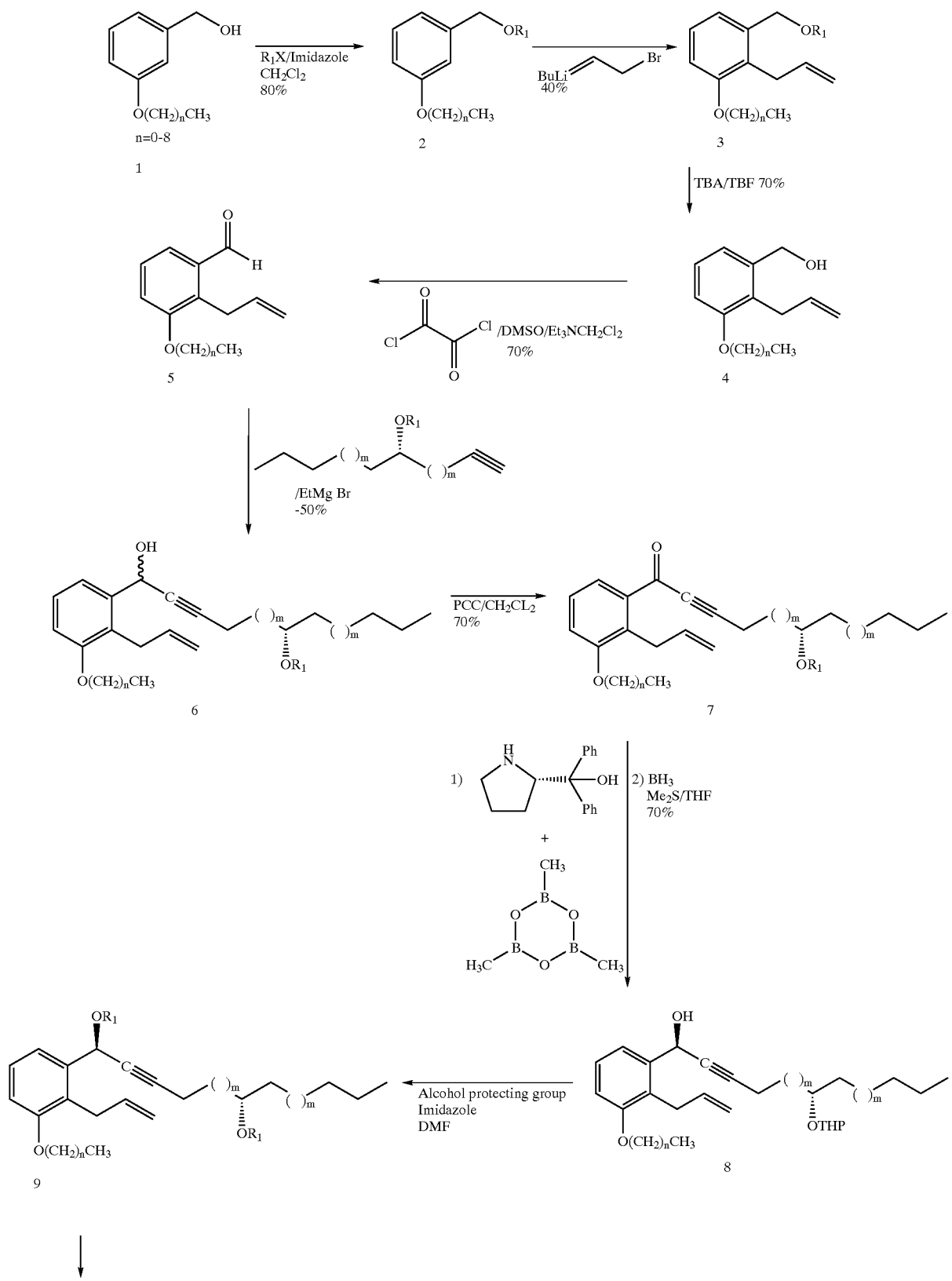

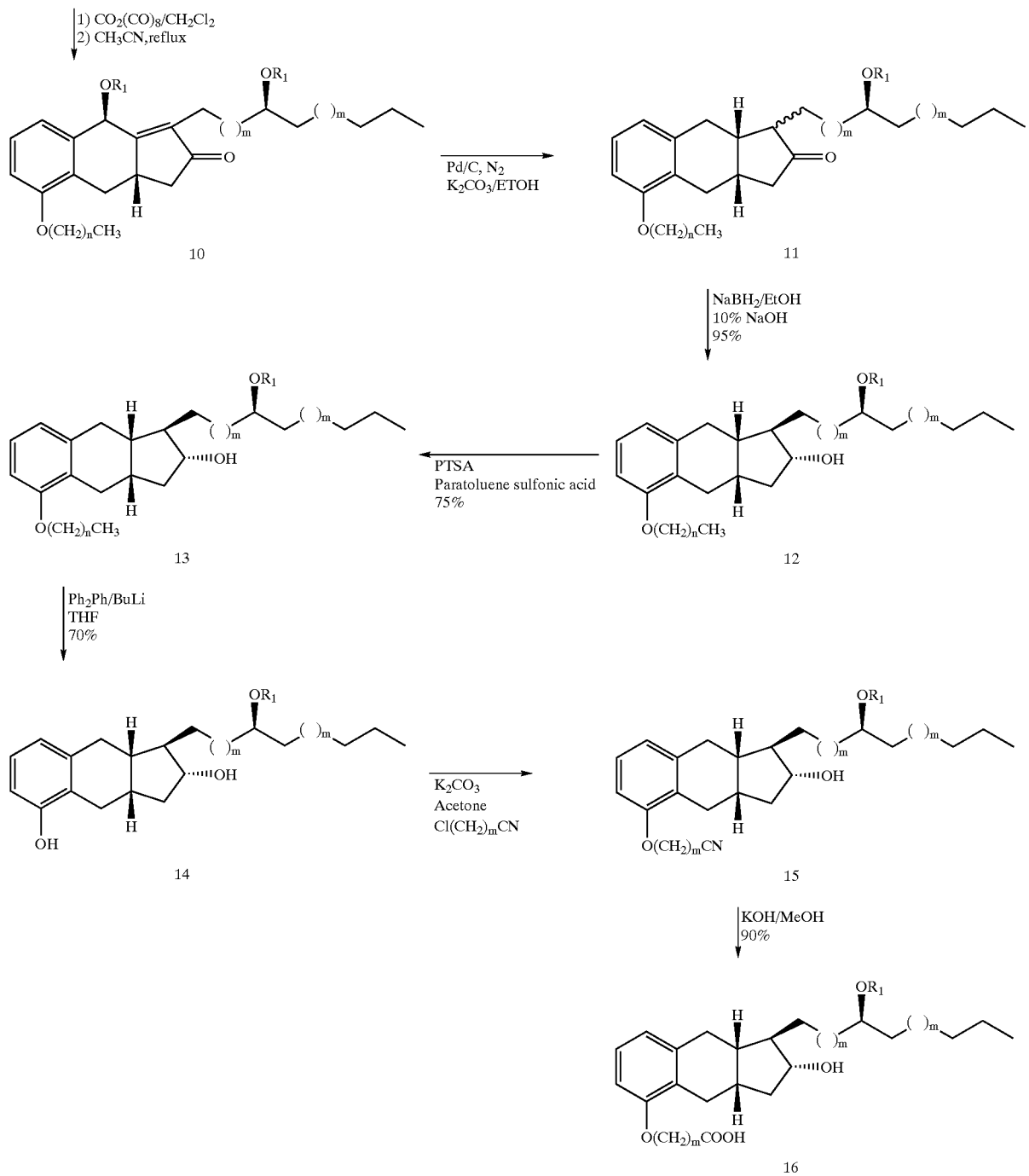

wherein $R_1$, is in each case an independently selected alcohol protecting group. Preferred alcohol protecting groups are tertiary butyl dimethyl sily (TBDMS) and tetra hydro pyranyl (THP).

The present invention also relates to the following novel intermediate compounds:

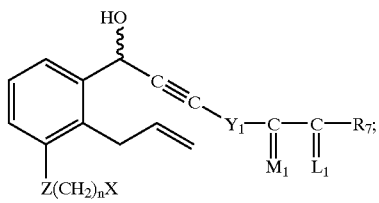

wherein X, Z, $Y_1$, $M_1$, $L_1$, $R_1$ and $R_7$ are as defined above.

The present invention is further illustrated by, though in no way limited to, the following examples.

EXAMPLE 1

9-Deoxy-2',9α-methano-3-oxa-4,5,6-trinor-3,7-(1', 3'-inter-phenylene)-13,14-dihydro-PGF$_1$

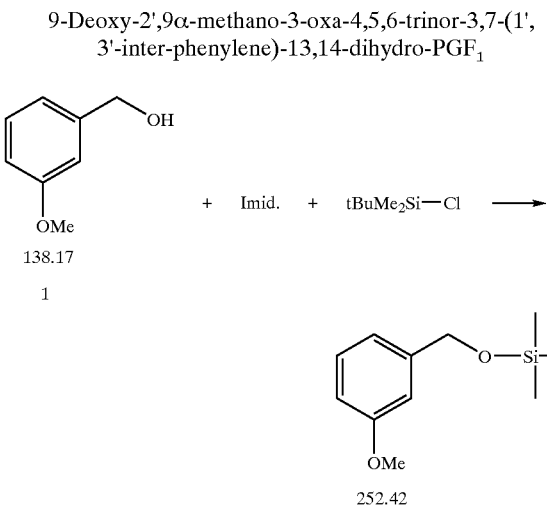

Procedure

To a solution of imidazole (29.6 g, 434 mmol, 2.8 eq.) in 1.0 L of methylene chloride were added 25 g (181 mmol) of 3-methoxybenzyl alcohol (1) in 200 ml of methylene chloride. After all material was dissolved, 32.7 g (217 mmol, 1.2 eq.) of t-butyldimethylsilyl chloride was added in portions. The reaction was stirred overnight at room temperature. The mixture was filtered and washed with water and then brine. The organic layer was separated, dried over MgSO$_4$, filtered, and evaporated to afford 53 g of a clear yellow oil that was used in the next step without further purification.

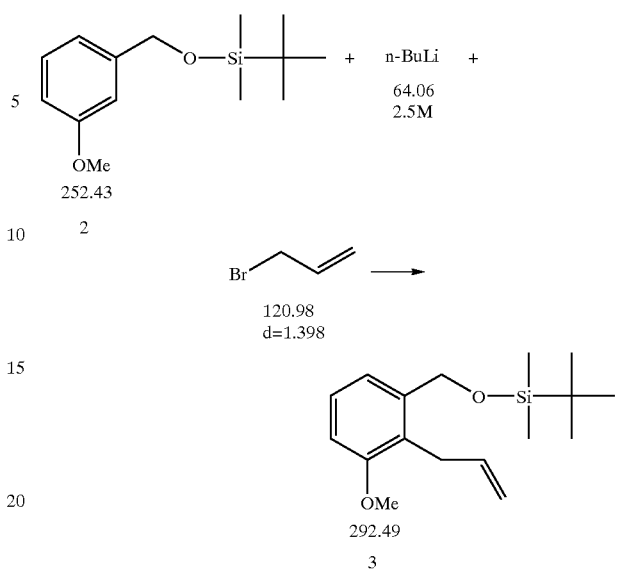

Procedure

To a solution of 95 g (376 mmol) of 2 dissolved in 400 ml of hexane under Ar at room temperature were added dropwise 26.5 g (414 mmol, 1.1 eq.) of BuLi in 166 ml of hexane. The mixture was stirred for 2 hours at room temperature, and then the reaction was cooled in an ice bath and 54.6 g (452 mmol) of allyl bromide were added dropwise. The reaction was allowed to warm to room temperature overnight. After stirring for 24 hours, TLC indicated 60% conversion, and the reaction was quenched with saturated NH$_4$Cl. The organic layer was separated and washed with Brine, dried over MgSO$_4$, and filtered. Evaporation of the solvent yielded a yellow oil which was used in the next reaction without further purification.

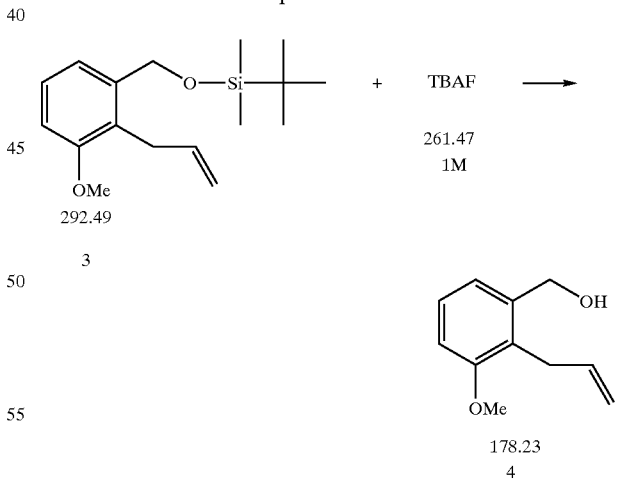

Procedure

To a solution 3 (110 g, 376 mmol) in 2.0 L of THF were added 128 g (489 mmol, 1.1 eq.) of tetrabutyl ammonium fluoride (TBAF) in 489 ml of THF. The reaction was stirred at room temperature and was complete after 4 hours. The reaction was quenched by adding 500 ml of water. The organic layer was separated and washed with brine and dried over MgSO₄. Filtration and evaporation of the solvent produced an orange oil which was purified by flash column chromatography, on silica gel using 10–30% ethyl acetate in hexanes as the eluent. The fractions containing the desired product were evaporated to afford 24 g (36% from 3-methoxybenzyl alcohol) of a yellow oil.

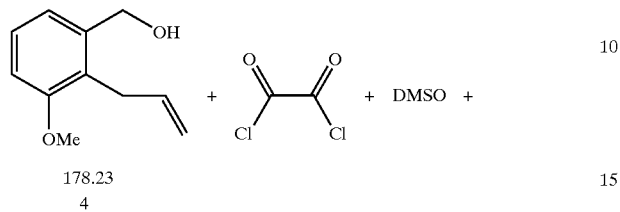

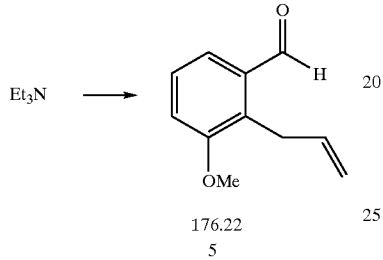

Procedures

To a solution of 20.6 g (162 mmol, 1.2 eq.) of oxalyl chloride in 250 ml of CH₂Cl₂ under Ar at −78° C. were added dropwise 24.2 g (310 mmol) of DMSO in 100 ml of CH₂Cl₂. After 10 minutes, 24 g (135 mmol) of 4 in 100 ml of CH₂Cl₂ were added dropwise. The mixture was stirred at −78° C. for 30 min., and then 68.3 g (675 mmol, 5.0 eq.) of Et₃N were added. Stirring continued as the reaction warmed to room temperature. The reaction was quenched with H₂O, washed with saturated NH₄Cl solution and Brine. The organic layer was separated and dried over MgSO₄. Filtration and evaporation of the solvent produced a brown oil which was purified by flash column chromatography, on silica gel using 5% ethyl acetate in hexanes as the eluent. The fractions containing the desired compound were evaporated to afford 20.5 g (86%) of a brown oil.

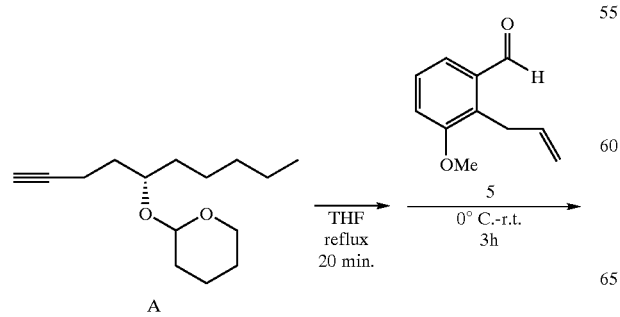

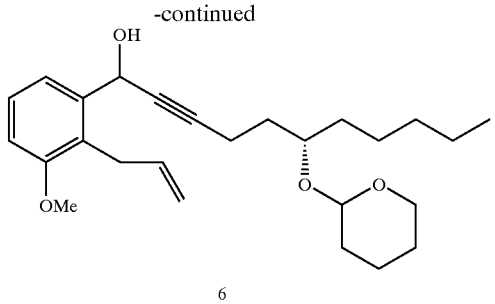

Procedure

Compound A may be synthesized according to S. Takano et al., Chemistry Lett., 1987, p. 2017. To a solution of side chain (A) (1.6 g, 6.72 mmol) in dry THF (10 ml) which was heated to gentle refluxing under argon was added EtMgBr (2.24 ml, 6.72 mmol, 3M solution). After the addition was complete, the resultant solution was refluxed for 20 min.

The solution was cooled to 0° C. (under argon) and a solution of 5 (1.183 g, 6.72 mmol) in THF (10 ml, dried over molecular sieves) was added dropwise with stirring. After the complete addition, the reaction mixture was allowed to warm to room temperature and stirred for 2–3 hrs. The reaction mixture was cooled to 0° C., diluted with saturated NH₄Cl solution, concentrated, extracted with ethyl acetate (4×25 ml), dried (MgSO₄) and the solvent distilled off in vacuo. The crude product (2.65 g) was purified by flash chromatography using 10–30% ether in hexane on silica gel to obtain a colorless oil 1.45 g (52%) of 6.

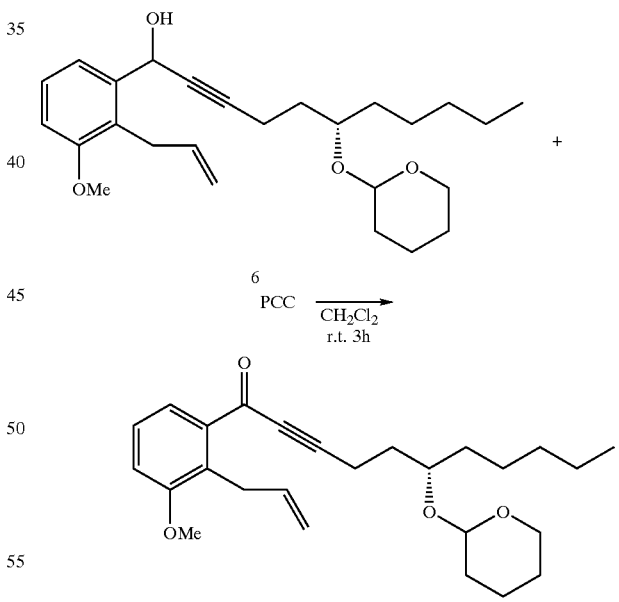

Procedure

To a solution of alcohol 6 (1.27 g, 13.07 mmol) in dry CH₂Cl₂ (20 ml) was added pyridinium chlorochromate (PCC) (1.32 g, 6.1:2 mmol) and the mixture was stirred at room temperature. PCC slowly dissolved and the color of solution turned orange-black after approx. 5 min. Stirring was continued for 3 hrs. The reaction mixture was diluted with ether (100 ml) and filtered through a plug of silica gel. The solid was washed 3 times with ether (3×50 ml). After the solvent was removed, the crude product (1.3 g) was purified by flash chromatography using 10% ether in hexane on silica gel to give 900 mg light yellow oil (71%).

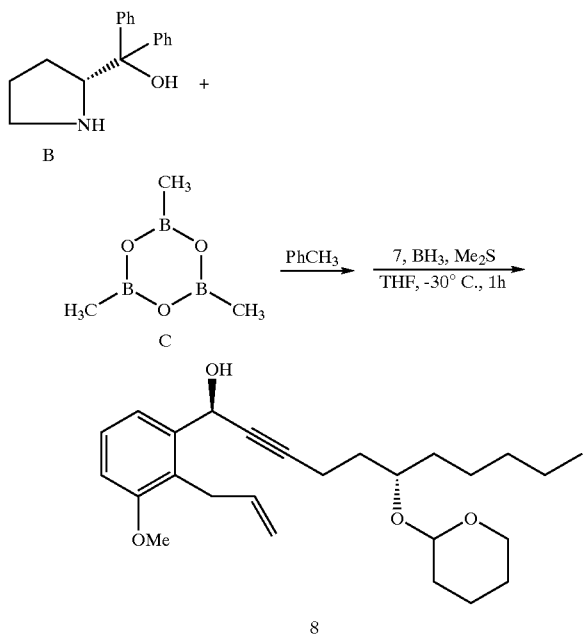

Procedure

STEP I:

Preparation of Reagent:

Compound B may be synthesized according to D. S. Mathre et al., J. Org. Chem. 1991, Vol. 56, p. 751; P. Beak, Org. Synth., 1997, p. 23. Compound B (1.08 g, 4.26 mmol) was dissolved in 30 ml of anh. toluene under argon. Trimethylboroxine (C) (0.357 g, 2.84 mmol) was added dropwise and the resulting solution was stirred at room temperature. White solid separated out after 3–4 min. After stirring for 30 min., toluene was distilled out at atmospheric pressure. Again 20 ml of dry toluene were added and distilled out. This distillation was repeated for 2 more times. The solution of reagent in toluene was allowed to cool under argon.

STEP II:

Reduction:

A solution of ketone 7 ( 0.88 g, 2.14 mmol) in dry THF (20 ml) was dried over molecular sieves for 2 hrs and added to the above reagent solution. The resulting solution was cooled to −30° C. ($CH_3CN$, $CO_2$) under argon and borane-methylsulfide complex (1.07 ml, 10.71 mmol) was added dropwise with stirring. After stirring at −30° C. for 1 hr, the reaction was quenched with methanol (10 ml), diluted with ether (100 ml), washed successively with saturated $NH_4Cl$, $NaHCO_3$ solution and brine, dried ($MgSO_4$) and concentrated in vacuo to yield a crude product (2.3 g). The crude product was purified by flash chromatography using 10% ether in hexane is on silica gel to give 770 mg of 8 as a colorless oil (87%).

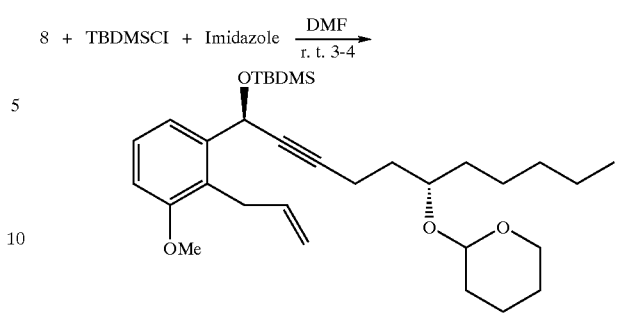

Procedure

TBDMSCl (0.337 g, 2.23 mmol) and imidazole (0.335 g, 4.65 mmol) were added to the solution of 8 (0.770 g, 1.86 mmol) in DMF (20 ml) at room temperature under argon, and the mixture was stirred at room temperature for 3–4 hrs. After the reaction was quenched with sat. $NH_4Cl$, the reaction mixture was extracted with ether (3×50 ml). The combined ether extracts were dried ($MgSO_4$) and concentrated in vacuo. The crude oil was purified by chromatography using 5% ether in hexane on silica gel to yield 860 mg of 9 as a colorless oil (88%).

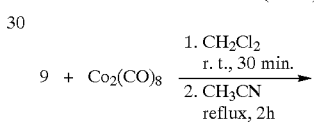

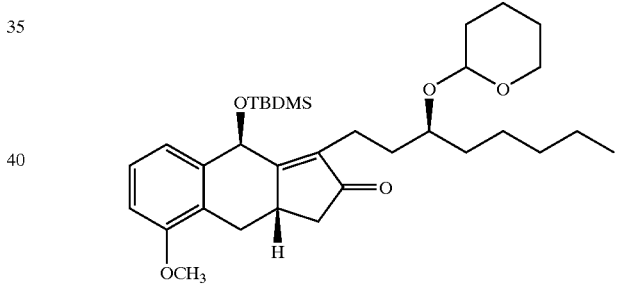

Procedure

STEP I:

Complex formation:

Compound 9 (0.840 g, 1.59 mmol) was dissolved in dry $CH_2Cl_2$ (15 ml) under argon, and $CO_2(CO)_8$ (0.653 g, 1.91 mmol) was added to it and stirred at room temperature under argon. carbon monoxide evolved out slowly, and the solution turned dark brown after 5 min. Stirring was continued for 30 min. at room temperature.

STEP II:

Pauson Khand Cyclization $CH_2Cl_2$ was distilled out from -the above solution. The complex was dissolved in dry $CH_3CN$ (50 ml), and the solution was refluxed under argon for 2 hrs. This solvent was distilled out, the crude mass was dissolved in ether and passed quickly through a short column of neutral alumina to yield 850 mg of light brown oil (96%).

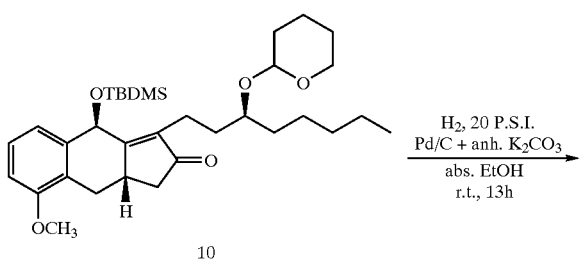

10

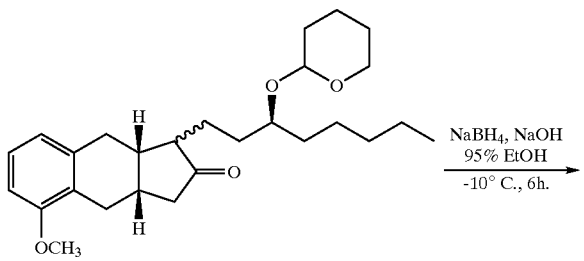

11

Procedure

Compound 10 (0.850 g, 1.53 mmol) was dissolved in absolute ethanol (50 ml). Anh. K₂CO₃ (0.020 g) and Pd/C (0.550 g, 10%D, wet) were added and the mixture was hydrogenated at 20 psi pressure for 13 hrs. The reaction mixture was filtered through celite and concentrated in vacuo. The crude product (800 mg) was purified by chromatography using 10–30% ether in hexane on silica gel to yield 440 mg of colorless oil (67%).

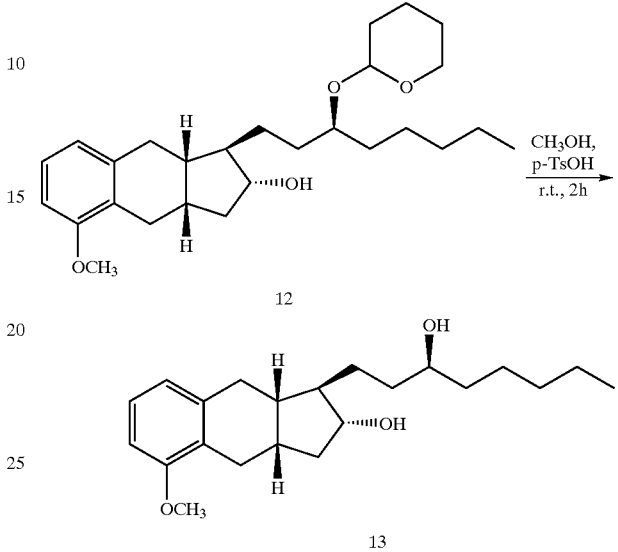

Procedure

A solution of ketone 11 (0.430 g) in 95% ethanol was cooled to –10° C. 10% NaOH (6 ml) and NaBH₄ (0.080 g) were added and the mixture was stirred at –10° C. for 1 hr. Then one more eq. of NaBH₄ (0.080 g) was added and stirring was continued for another 5 hrs. at –10° C. After quenching carefully with glacial acetic acid, the solvent was removed under reduced pressure. Resulting oil was dissolved in ethyl acetate, washed with aq. NaHCO₃, brine, dried (MgSO₄) and concentrated in vacuo to obtain 430 mg of colorless oil (98%) which has a single spot on TLC. Further purification was not required.

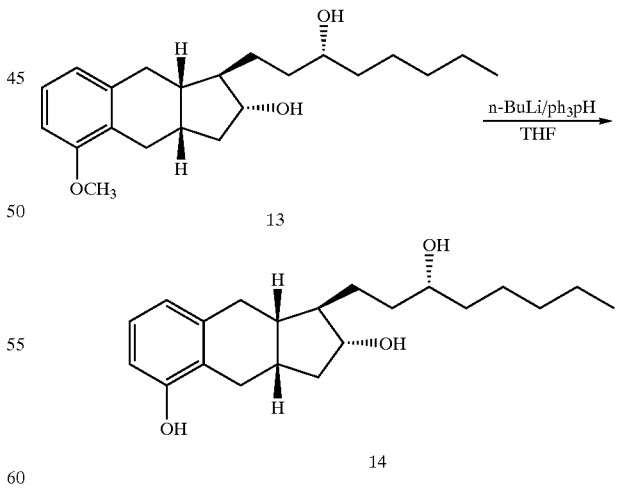

Procedure

To 400 mg (0.93 mmol) of compound 12 dissolved in methanol (10 ml) was added p-TsOH (20 mg), and the solution Was stirred at room temperature until TLC showed completion of the reaction (2 hrs). The solvent was removed in vacuo, the residue was dissolved in CH₂Cl₂, washed with sat. NaHCO₃, dried(MgSO₄), and concentrated in vacuo. The crude product was purified by silica gel column chromatography (30% ether in hexanes as eluent) to give 250 mg 13 (78%).

Procedure n-BuLi (1.1 ml, 1.72 mmol)(1.6 M in hexanes) was added dropwise to a cold (–20° C.) and stirred solution of diphenylphosphine (0.28 g, 1.5 mmol) in anhydrous THF (8 ml) under argon. The reaction mixture was warmed to room temperature (20° C.). A solution of diol (13) (0.17 g, 0.49 mmol) in dry THF (0.6 ml) was added dropwise to the reaction mixture and the whole solution was heated to reflux for 3 hrs (TLC shows starting material), heating was stopped and the reaction mixture was cooled again to −20° C. and diphenylphosphine (0.37 g, 1.96 mmol) was added followed by dropwise addition of n-BuLi (1.5 ml, 2.38 mmol)(1.6M in hexanes) under argon. After complete addition, the reaction mixture was warmed to 20° C. and then refluxed for 18 hrs. TLC shows 80–90% conversion (14). The reaction mixture was cooled to −5° C. and then an aqueous solution of NaCl containing 5% conc. HCl was added dropwise to quench the reaction. The reaction mixture was extracted with ethyl acetate 3×20 ml and the combined organic layers were washed with brine and dried (Na$_2$SO$_4$), filtered and concentrated. The crude product was purified by silica gel column chromatography (50% EtOAc/Hex. as eluent) to give 0.12 g of product (75%) (22 mg of starting diol was recovered).

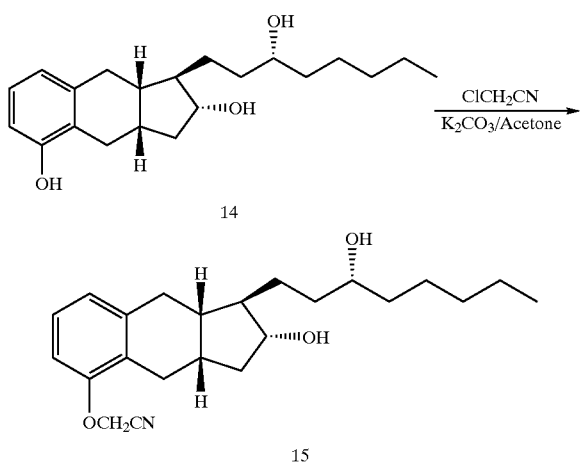

14

15

Procedure

A suspension of compound (14) (0.12 g. 0.37 mmol), chloroacetonitrile (0.56 g, 7.4 mmol) and K$_2$CO$_3$ (0.51 g, 3.7 mmol) in dry acetone (15 ml) was refluxed under Ar for 20 hrs. The reaction mixture was cooled to room temperature and celite (0.5 g) was added. After the mixture was filtered, the solvent was removed under reduced pressure. The crude product was purified by silica gel column chromatography using 1:1 EtOAc/hexanes as eluent to yield 0.12 g of product (95%).

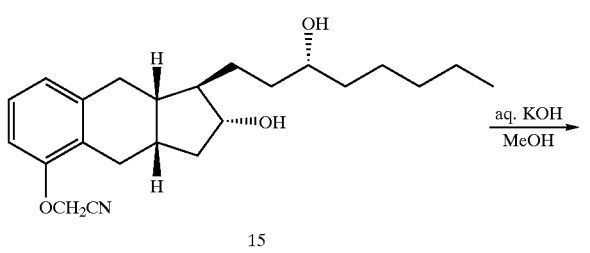

15

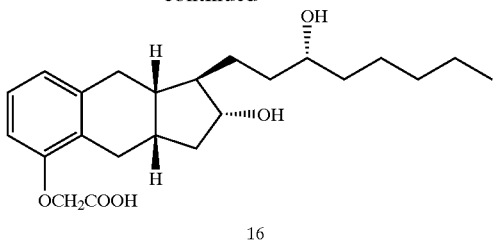

16

Procedure

Aqueous KOH (0.4 g, 7.12 mmol, water 1.2 ml, 35% solution) was added dropwise to a stirred solution of nitrile compound (15) (0.072 g, 0.21 mmol) in methanol (4 ml) and the reaction mixture was refluxed for 3 hrs. The reaction mixture was cooled to 10° C., dilute aqueous HCl was added to pH 8 and the solvent was removed in vacuo. Ethyl acetate (20 ml) and aqueous NaCl solution (10 ml) were added and the pH of the reaction mixture was acidified to between 2 and 3 by addition of 2% HCl. The reaction mixture was extracted with ethyl acetate (2×20 ml). The combined ethyl acetate extracts were washed with brine, dried (Na$_2$SO$_4$) and concentrated under reduced pressure. The crude product was purified by silica gel column chromatography using a dichloromethane solution containing 3% methanol and 0.1% acetic acid as eluent to yield 0.076 g of product (95%).

It will be apparent to those skilled in the art that various modifications and variations can be made to the processes and novel intermediates of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A process for making 9-deoxy-PGF$_1$-type compounds comprising cyclizing a starting compound of the formula:

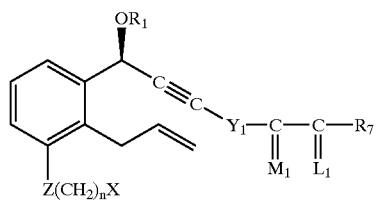

into a compound of the following formula:

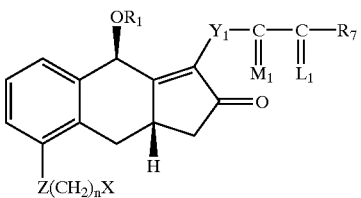

by cobalt mediated cyclization wherein the starting compound is reacted with CO$_2$(CO)$_8$, wherein Z is O, S, CH$_2$, or NR$_8$ in which R$_8$ is H, alkyl or aryl;

X is H, CN, $OR_9$, or $COOR_9$ in which $R_9$ is alkyl, THP or TBDMS;
wherein n is 0, 1, 2, or 3;
wherein $Y_1$ is trans-CH=CH—, cis-CH=CH—, —$CH_2(CH_2)_m$—, or —C≡C—; m is 1,2, or 3;
wherein $R_1$ is an alcohol protecting group;
wherein $R_7$ is
(1) —$C_pH_{2p}$—$CH_3$, wherein p is an integer from one to 5, inclusive,
(2) phenoxy optionally substituted by one, two or three chloro, fluoro, trifluoromethyl, ($C_1$–$C_3$)alkyl, or

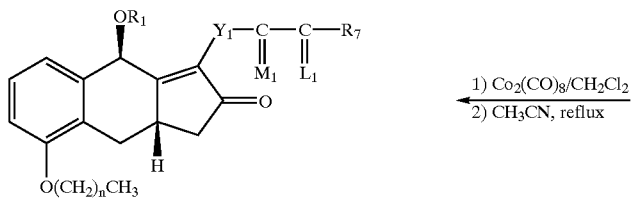 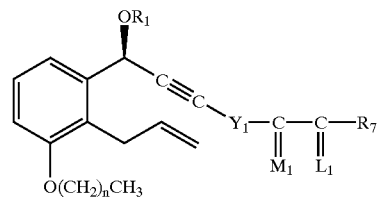

($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$–$C_3$) alkyl, or ($C_1$–$C_3$)alkoxy, with the proviso that not more than two substituents are other than alkyl,
(4) cis-CH=CH—$CH_2$—$CH_3$,
(5) —$(CH_2)_2$—CH(OH)—$CH_3$, or
(6) —$(CH_2)_3$—CH=C$(CH_3)_2$;
wherein —C($L_1$)—$R_7$ taken together is
(1) ($C_4$–$C_7$)cycloalkyl optionally substituted by one to 3 ($C_1$–$C_5$) alkyl;
(2) 2-(2-furyl)ethyl,
(3) 2-(3-thienyl)ethoxy, or
(4) 3-thienyloxymethyl;
wherein $M_1$ is α-OH:β-$R_5$ or α-$R_5$:β-OH or α-$OR_1$:β-$R_5$ or α-$R_5$:β-$OR_1$, wherein $R_5$ is hydrogen or methyl and $R_1$ is an alcohol protecting group; and
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

2. The process as claimed in claim 1, wherein the cyclization is a cobalt-mediated cyclization.

3. The process as claimed in claim 2, wherein the starting compound is reacted with $Co_2(CO)_8$ in a non-reactive solvent to form a complex, followed by heating to form the tricyclic compound.

4. The process as claimed in claim 3, wherein the non-reactive solvent during the complex-forming step is $CH_2Cl_2$ and the non-reactive solvent during the heating step is $CH_3CN$.

5. The process as claimed in claim 3, wherein the non-reactive solvent during the complex-forming step is toluene and the non-reactive solvent during the heating step is toluene.

6. A stereoselective process of making a 9-deoxy-$PGF_1$-type compound, comprising the following reaction:

wherein $R_1$ is an alcohol protecting group;
wherein n is 0, 1, 2, or 3;
wherein $Y_1$ is trans-CH=CH—, cis-CH=CH—, —$CH_2(CH_2)_m$—, or —C≡C—; m is 1,2, or 3;
wherein $R_7$ is
(1) —$C_pH_{2p}$—$CH_3$, wherein p is an integer from one to 5, inclusive,
(2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$–$C_3$) alkyl, or ($C_1$–$C_3$)alkoxy, with the proviso that not more than two substituents are other than alkyl,
(4) cis-CH=CH—$CH_2$—$CH_3$,
(5) —$(CH_2)_2$—CH(OH)—$CH_3$, or
(6) —$(CH_2)_3$—CH=C$(CH_3)_2$;
wherein —C($L_1$)—$R_7$ taken together is
(1) ($C_4$–$C_7$)cycloalkyl optionally substituted by one to 3 ($C_1$–$C_5$) alkyl;
(2) 2-(2-furyl)ethyl,
(3) 2-(3-thienyl)ethoxy, or
(4) 3-thienyloxymethyl;
wherein $M_1$ is α-OH:β-$R_5$ or α-$R_5$:β-OH, wherein $R_5$ is hydrogen or methyl;
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

7. The process as claimed in claim 6, further comprising the following steps:

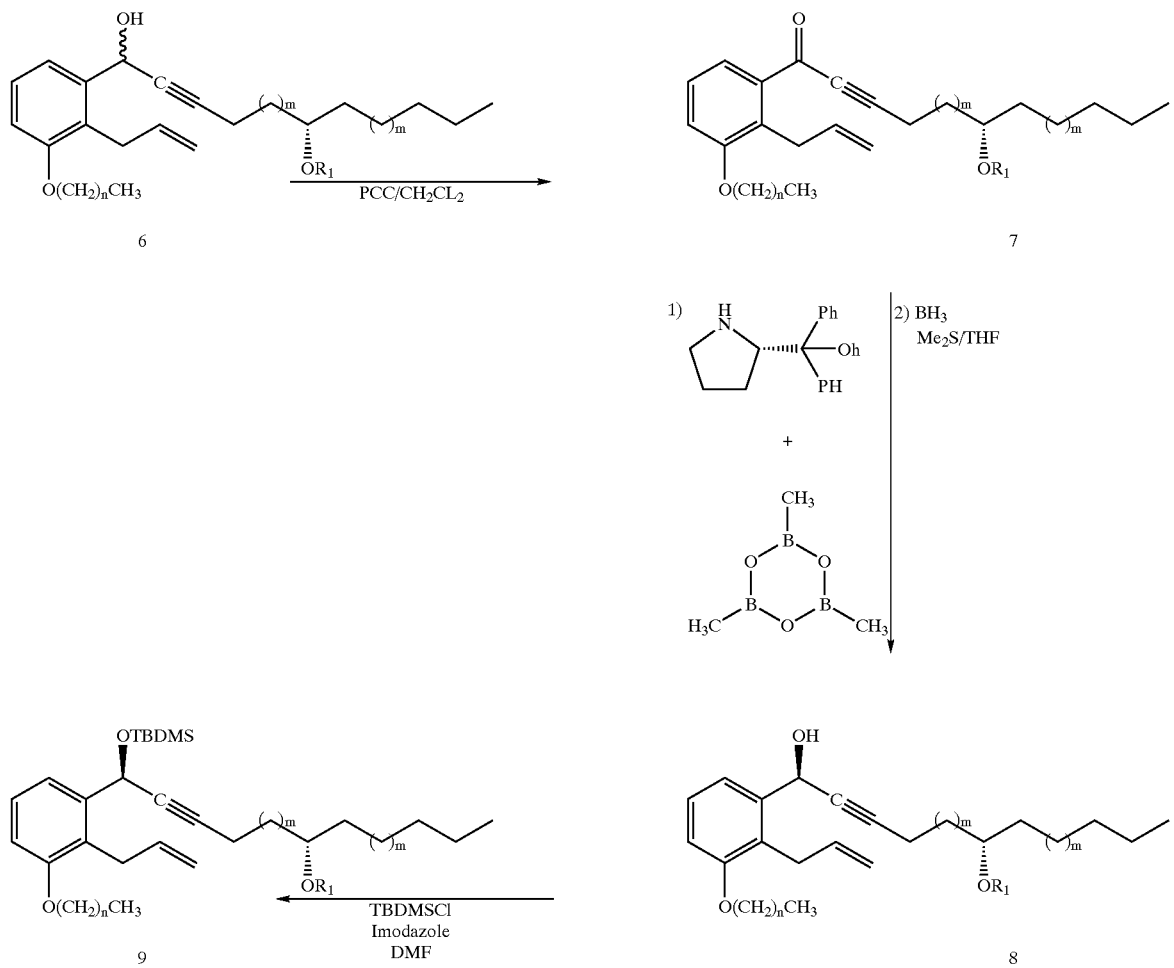
wherein $R_1$ is an independently selected alcohol protecting group, m is 1, 2, or 3 and n is 0, 1, 2, or 3.
8. The process as claimed in claim 7, comprising the following steps:
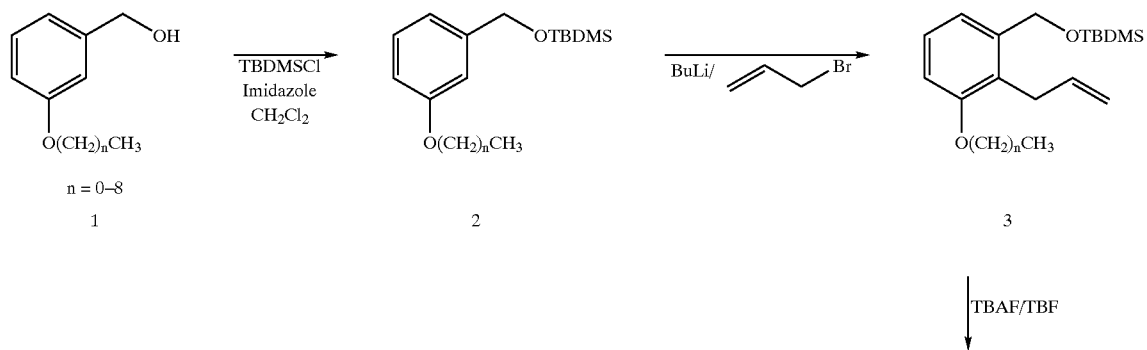

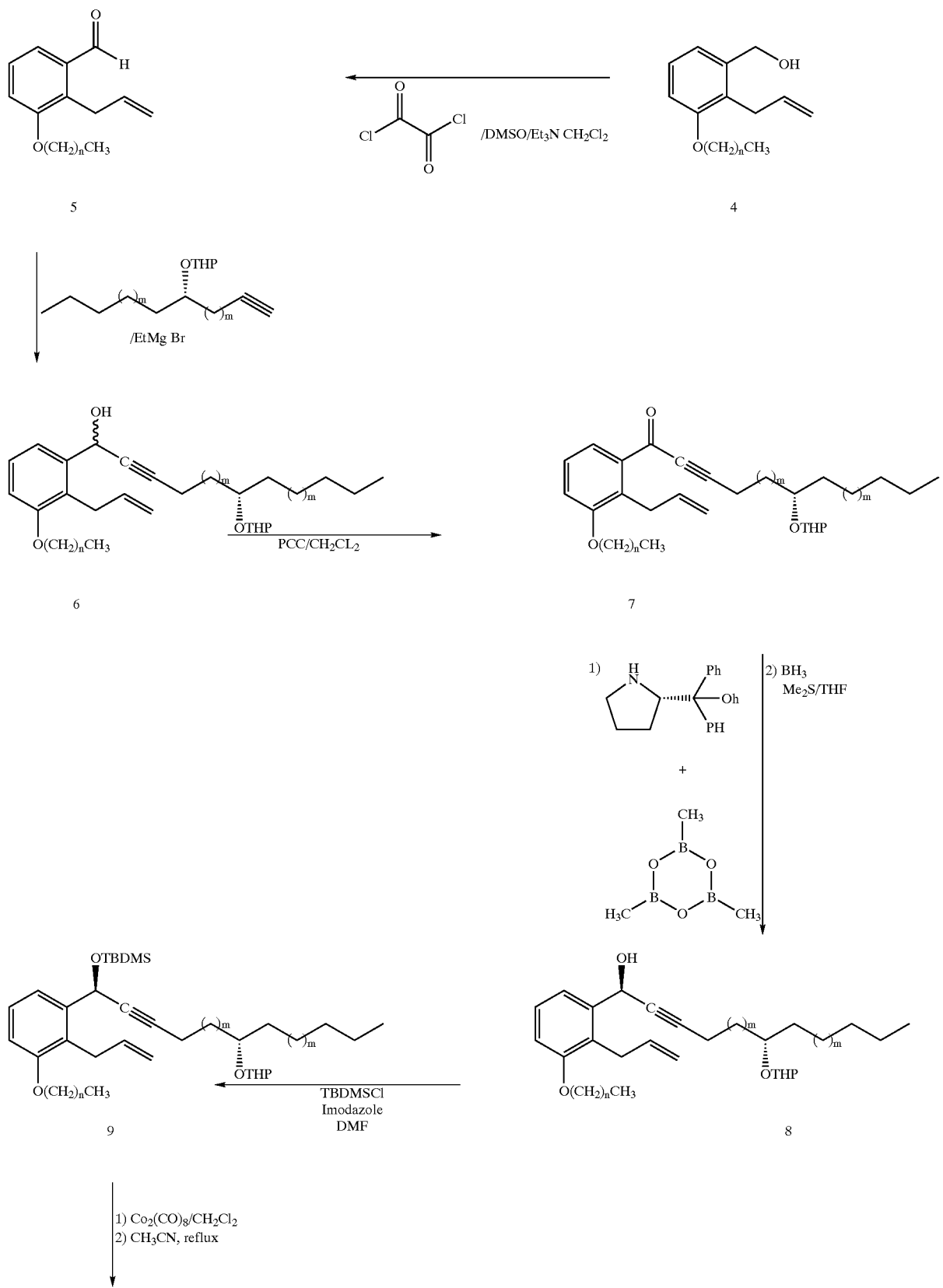

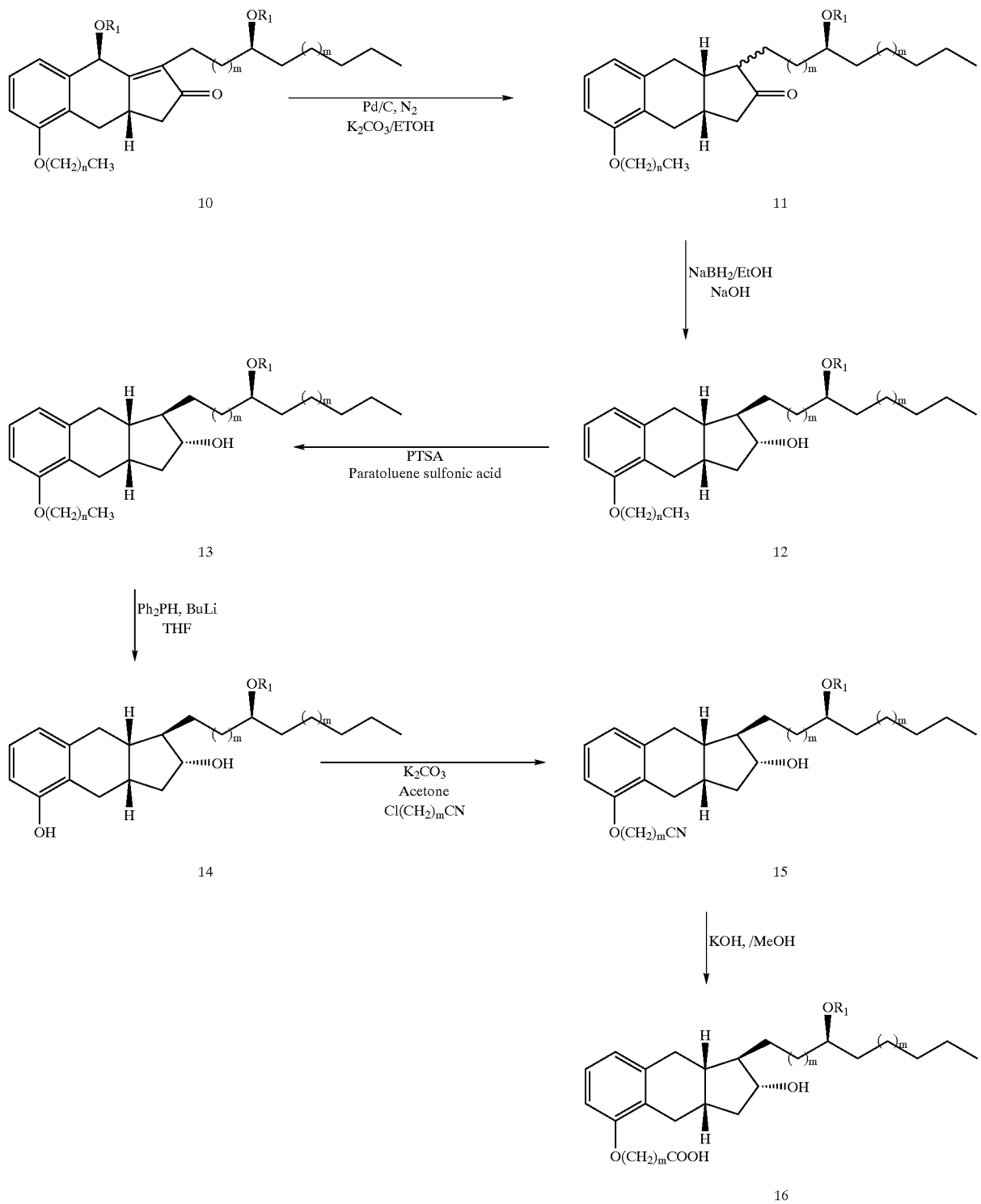

9. The process as claimed in claim 8, wherein m is 1 and n is 0.

10. A compound of the formula

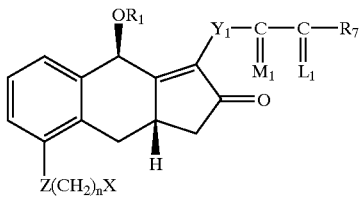

wherein Z is O, S, $CH_2$, or $NR_8$ in which $R_8$ is H, alkyl or aryl;

wherein X is H, CN, $OR_9$, or $COOR_9$ in which $R_9$ is alkyl, THP or TBDMS;

wherein $R_1$ is an alcohol protecting group;

wherein n is 0, 1, 2, or 3;

wherein $Y_1$ is trans-CH=CH—, cis-CH=CH—, —$CH_2$$(CH_2)_m$—, or —C≡C—; m is 1, 2, or 3;

wherein $R_7$ is
(1) —$C_pH_{2p}$—$CH_3$, wherein p is an integer from one to 5, inclusive,
(2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$–$C_3$) alkyl, or ($C_1$–$C_3$)alkoxy, with the proviso that not more than two substituents are other than alkyl,
(4) cis-CH=CH—$CH_2$—$CH_3$,
(5) —$(CH_2)_2$—CH(OH)—$CH_3$, or
(6) —$(CH_2)_3$—CH=C$(CH_3)_2$;

wherein —C($L_1$)—$R_7$ taken together is
(1) ($C_4$–$C_7$)cycloalkyl optionally substituted by one to 3 ($C_1$–$C_5$)alkyl;
(2) 2-(2-furyl)ethyl,
(3) 2-(3-thienyl)ethoxy, or
(4) 3-thienyloxymethyl;

wherein $M_1$ is α-OH:β-$R_5$ or α-$R_5$:β-OH, wherein $R_5$ is hydrogen or methyl;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

* * * * *